United States Patent [19]

Barns et al.

[11] Patent Number: 5,663,049
[45] Date of Patent: Sep. 2, 1997

[54] DETECTION OF CAMPYLOBACTER

[75] Inventors: Susan M. Barns, Hopkinton; Ray A. McMillian, Shrewsbury; David J. Lane, Milford; Mark L. Collins, Holden; James E. Awell, Norfolk, all of Mass.; Ayoub Rashtchian, Gaithersburg, Md.

[73] Assignee: Amoco Corporation, Chicago, Ill.

[21] Appl. No.: 453,756

[22] Filed: May 30, 1995

Related U.S. Application Data

[60] Division of Ser. No. 216,679, Jul. 7, 1988, Pat. No. 5,447,848, which is a continuation-in-part of Ser. No. 821,393, Jan. 22, 1986, abandoned.

[51] Int. Cl.$^6$ .............. C12Q 1/68; C07H 21/02; C07H 21/04
[52] U.S. Cl. .............. 435/6; 536/23.1; 536/24.3
[58] Field of Search ............... 435/6; 536/23.1, 536/24.3

[56] References Cited

U.S. PATENT DOCUMENTS

| | | | |
|---|---|---|---|
| 4,358,535 | 11/1982 | Falkow et al. | 435/5 |
| 4,689,295 | 8/1987 | Tabor et al. | |
| 4,785,086 | 11/1988 | Rachtchian et al. | |
| 5,447,848 | 9/1995 | Barns et al. | 435/6 |

FOREIGN PATENT DOCUMENTS

| | | |
|---|---|---|
| 0 155 360 | 9/1985 | European Pat. Off. . |
| 232085 | 8/1987 | European Pat. Off. . |
| 350205 | 1/1990 | European Pat. Off. . |
| 84/02721 | 7/1984 | WIPO . |
| 03957 | 6/1988 | WIPO . |

OTHER PUBLICATIONS

Arden et al., *Nature*, 316:783–787 (1985).
Carr et al., *Gene*, 48:257–266 (1986).
Fukusaki et al, *FEBS Lett.*, 17(2):197–201 (1984).
Kitamura et al., *Nature*, 297:205–208 (1982).
Leaper et al., *FEMS Microbiol. Lett.*, 15:203–208 (1982).
LeBon et al., *DNA*, 4(1):96 (Feb. 1986).
Paster et al., *Int'l J. Systematic Bacteriol.*, 38:56–62 (Jan. 1988).
Romaniuk et al., *FEMS Microbiol. Lett.*, 43:331–335 (1987).
Thompson III et al., *Int'l Systematic Bacteriol.*, 38:190–200 (Apr. 1988).

*Primary Examiner*—W. Gary Jones
*Assistant Examiner*—Ethan Whisenant
*Attorney, Agent, or Firm*—Norval B. Galloway

[57] ABSTRACT

The invention relates to methods of using nucleic acid probes capable of specifically hybridizing to rRNA of *Campylobacter jejuni*, *C. coli* and *C. laridis* and not to rRNA or rRNA genes of *Pseudomonas aeruginosa*, *E. coli* or *Salmonella typhimunium* for the detection of Campylobacter in clinical, food and other samples.

16 Claims, No Drawings

DETECTION OF CAMPYLOBACTER

RELATED APPLICATION

This application is a divisional application of commonly assigned, application, U.S. Ser. No. 07/216,679, filed Jul. 7, 1988, now issued U.S. Pat. No. 5,447,848, which is a continuation-in-part application of commonly assigned, copending application, U.S. Ser. No. 06/821,393, filed Jan. 22, 1986, now abandoned.

FIELD OF THE INVENTION

This invention relates to detecting bacteria belonging to the genus Campylobacter and more specifically provides nucleic acid probes and compositions along with methods for their use for the specific detection of rRNA or rRNA genes of Campylobacter.

Background of the Invention

The term "Campylobacter" as used herein, refers to the bacteria classified as such in Bergey's Manual of Systematic Bacteriology, Vol. 1 (N. R. Krieg and J. G. Holt [eds.], 1986, pp. 111–118, Williams & Wilkins). Detection of Campylobacter is important in various medical and public health contexts. Campylobacter jejuni and C. coli are the two most important species, causing diarrhea (Blaser et al., 1979, Ann. Intern, Med. 91:179), and enteriris (G. K. Morris et al., eds, American Society for Microbiology, Washington, D.C.) in humans. Other Campylobacter species have been implicated in causing disease in humans or animals, such as abortion, septicemia and proliferative ileitis. In addition, microorganisms resembling Campylobacter have been isolated from feces of homosexual men (Fennell et al., 1984 J. Infec. Dis. 149:58) and from gastric ulcer biopsies (Kasper et al., 1984 Infection. 12:179).

It is, therefore, an aspect of the present invention to provide a novel assay system capable of rapidly detecting Campylobacter and which is generally applicable to environmental, food or clinical samples.

Campylobacter generally are identified pursuant to a standard laboratory method (Campylobacter, In Washington, J. A. [ed.], Laboratory Procedures in Clinical Microbiology, 2nd Ed., New York, Springer-Verlag, 1985, pp. 215–217).

It is yet another aspect of the present invention to avoid the disadvantages associated with traditional culturing techniques and to employ nucleic acid probes to detect Campylobacter.

It is yet another aspect of the present invention to provide probes which can hybridize to target regions which can be rendered accessible to the probes under normal assay conditions.

While Kohne et al. (1968, Biophysical Journal 8:1104–1118) discuss one method for preparing probes to rRNA sequences they do not provide the teaching necessary to make Campylobacter-specific probes.

Pace and Campbell (1971, Journal of Bacteriology 107:543–547) discuss the homology of ribosomal ribonucleic acids from diverse bacterial species and a hybridization method for quantitating such homology levels. Similarly, Sogin, Sogin, and Woese (1972, Journal of Molecular Evolution 1:173–184) discuss the theoretical and practical aspects of using primary structural characterization of different ribosomal RNA molecules for evaluating phylogenetic relationships.

Fox, Pechman, and Woese (1977, International Journal of Systematic Bacteriology 27:44–57) discuss the comparative cataloging of 16S ribosomal RNAs as an approach to prokaryotic systems. These references, however, fail to relieve the deficiency of Kohne's teaching with respect to Campylobacter.

Rashtchian and Fitts in copending application U.S. Ser. No. 692,778 discuss the generation of certain Campylobacter-specific nucleic acid probes targeted at genomic DNA sequences, but the method described would not yield small oligonucleotide probes.

It is yet another aspect to provide small oligonucleotide probes capable of specifically detecting Campylobacter. Romaniuk et al. (1987, J. Bacteriol. 169:2137–2141), Rashtchian et al. (1987, Current Microbiol. 14:311–317), Lau et al. (1987, System and Appl. Microbiol. 9:231–238), Paster and Dewhirst (1988, Intnl. J. System. Bacteriol. 38:56–62), and Thompson et al. (1988, Intnl. J. System. Bacteriol. 38:190–200) discuss Campylobacter ribosomal RNA gene organization and present 16S rRNA sequences from various Campylobacter. The references, however, fail to identify to probe target regions of most interest.

Romaniuk and Trust (1987, FEMS Microbiol. Lett. 43:331–335), describe an oligonucleotide probe which hybridizes to a region of Campylobacter 16S rRNA and demonstrates its use in identifying strains of Campylobacter by Southern hybridization to electrophoretically-separated restriction fragments of Campylobacter genomic DNA. While useful in this limited context, this probe does not have sufficient specificity to identify Campylobacter in samples containing mixed populations of Campylobacter and non-Campylobacter bacteria.

Ribosomes are of profound importance to all organisms because they serve as the only Known means of translating genetic information into cellular proteins, the main structural and catalytic elements of life. A clear manifestation of this importance is the observation that all cells have ribosomes.

Ribosomes contain three distinct RNA molecules which, at least in E. coli, are referred to as 5S, 16S, and 23S rRNAs. These names historically are related to the size of the RNA molecules, as determined by sedimentation rate. In actuality, however, they vary substantially in size between organisms. Nonetheless, 5S, 16S, and 23S rRNA are commonly used as generic names for the homologous RNA molecules in any bacteria, and this convention will be continued herein.

Hybridization is traditionally understood as the process by which, under predetermined reaction conditions, two partially or completely complementary single-stranded nucleic acids are allowed to come together in an antiparallel fashion to form a double-stranded nucleic acid with specific and stable hydrogen bonds. The stringency of a particular set of hybridization conditions is defined by the base composition of the probe/target duplex, as well as by the level and geometry of mispairing between the two nucleic acids. Stringency may also be governed by such reaction parameters as the concentration and type of ionic species present in the hybridization solution, the types and concentrations of denaturing agents present, and/or the temperature of hybridization. Generally, as hybridization conditions become more stringent, longer probes are preferred if stable hybrids are to be formed. As a corollary, the stringency of the conditions under which a hybridization is to take place (e.g., based on the type of assay to be performed) will largely dictate the preferred probes to be employed. Such relationships are well understood and can be readily manipulated by those skilled in the art. As a general matter, dependent upon probe length, such persons understand stringent conditions to mean approximately 35° C.–65° C. in a salt solution of approximately 0.9 molar.

As used herein, probe(s) refer to synthetic or biologically produced nucleic acids (DNA or RNA) which, by design or selection, contain specific nucleotide sequences that allow them to hybridize under defined predetermined stringencies, specifically (i.e., preferentially) to target nucleic acid sequences.

A target nucleic acid sequence is one to which a particular probe is capable of preferentially hybridizing.

Still other useful definitions are given as their first use arises in the following text. All references cited herein are fully incorporated by reference.

SUMMARY OF THE INVENTION

In accordance with the various principles and aspects of the present invention, there are provided nucleic acid probes and probe sets comprising DNA or RNA sequences which, under specific hybridization conditions, are capable of detecting the presence of ribosomal RNA (rRNA) molecules of *Campylobacter jejuni, C. coli* and *C. laridis*, but which are not capable, under the same conditions, of detecting the rRNA of other related bacteria which may be present in the test sample. Relevant test samples might include for example, feces, blood, or other body fluids or tissues as well as foods and biological samples or materials from animals.

The probes of the instant invention can be used to identify a number of genetically distinct groups of Campylobacter. These are shown in Table 1 and indicated by boxes surrounding the major groupings. Within these groups, some further subdivision is possible and is indicated by spacing between the subgroups. *C. jejuni, C. coli* and *C. laridis*—the Campylobacter species which account for the vast majority of isolates from clinical (stool) specimens and contaminated foods—form a discrete group. They are closely related to one another and distinct (in the pattern and extent of 16S rRNA nucleotide sequence variation) from the other Campylobacter species. Intermixed among the other three Campylobacter groups are a number of non-Campylobacter bacteria including representatives of the genera Wolinella, Bacteroides, Thiovulum and Flexispira (see Table 1).

The probes described herein hybridize principally with the members of the *C. jejuni, C. coli* and *C. laridis* group. Because of their overwhelming prevalence compared to other Campylobacter species in the clinical, food and environmental samples of most interest, and because of their genetic distinctness, probes specific for this Campylobacter group are of primary importance.

The present invention also features an assay system for the utilization of these probes, the preferred format of which can advantageously enhance the aforementioned desirable behavior of the probes. The assay system of the present invention advantageously exhibits the following enhanced performance capabilities with respect to other currently available means for detection of Campylobacter:

a) increased sensitivity; i.e., the ability to detect Campylobacter in a given sample more frequently than currently available methods;

b) potentially significant reductions in assay cost due to the use of inexpensive reagents and reduced labor;

c) accurate identification of even biochemically unusual Campylobacter; and d) faster results because the test may be performed on uncultured samples which need not be grown further. Accordingly, the preferred test of this invention advantageously takes only one day to provide results.

It has been discovered that other advantages incurred by directing the probes of the present invention against rRNA include the fact that the rRNAs detected constitute a significant component of cellular mass. Although estimates of cellular ribosome content vary, actively growing Campylobacter bacteria may contain upwards of $5.0 \times 10E+3$ ribosomes per cell, and therefore $5.0 \times 10E+3$ copies of each of the rRNAs (present in a 1:1:1 stoichiometry in ribosomes). In contrast, other potential cellular target molecules such as genes or RNA transcripts thereof, are less ideal since they are present in much lower abundance.

A further unexpected advantage is that the rRNAs (and the genes encoding them) appear not to be subject to lateral transfer between contemporary organisms. Thus, the rRNA primary structure provides an organism-specific molecular target, rather than a gene-specific target as would likely be the case, for example, of a plasmid-borne gene or product thereof which may be subject to lateral transmission between contemporary organisms.

Additionally, the present invention provides probes to Campylobacter rRNA target sequences which are capable of distinguishing between a number of Campylobacter (described above). A preferred mixture of two probes also is provided which can hybridize to the rRNA target regions of *Campylobacter jejuni, C. coli* and *C. laridis*, the Campylobacter species most commonly isolated from clinical, food and environmental samples. Advantageously, these same rRNA target sequences are sufficiently different in most non-Campylobacter rRNAs that, under the preferred assay conditions of the present invention, the probe(s) of the present invention hybridize to Campylobacter rRNAs and do not generally hybridize to non-Campylobacter rRNAs. These probe characteristics are defined as inclusivity and exclusivity, respectively. The discovery that probes could be generated with the extraordinary inclusivity and exclusivity characteristics of those of the present invention with respect to Campylobacter was unpredictable and unexpected.

In a particularly preferred embodiment of the invention, an assay method for detecting *Campylobacter jejuni, C. coli* and *C. laridis* in stool specimens is provided. The test is rapid, sensitive and non-isotopic, does not require cultivation of bacteria in the sample prior to the hybridization step, and is highly specific for the mentioned Campylobacter.

BRIEF DESCRIPTION OF THE TABLES

Further understanding of the principles and aspects of the present invention may be made by reference to the tables wherein:

Table 1 Shows the relationships among a number of subgroups of Campylobacter species which have been discovered based on analysis of the patterns of sequence variations that exist in Campylobacter 16S rRNAs. This table provides a useful framework for understanding the specificity (inclusivity) of the various probes and probe sets disclosed herein; and Tables 2a–d Shows alignment of the nucleotide sequences of the probes of the present invention with their nucleotide target sequences of Campylobacter 16S rRNA (using the *E. coli* position numbering convention, Brosius et al., 1978, Proc. Natl. Acad. Sci. USA 75:4801–4805) along with relevant portions of the 16S rRNAs from other related bacteria including Wollinella, Bacteroides, Flexispira and Thiovulum. The *E. coli* sequence also is shown for the purpose of identifying the positions of the target regions. RNA sequences are written 5' to 3', probe sequences are DNA and written 3' to 5'. Lower case c in certain of the probes indicates a modified cytosine residue to which a reporter group may or may not be attached depending on the assay form employed; and Table 3 Exemplifies the inclusivity and exclusivity behavior of the preferred probes toward a representative sampling of Campylobacter and non-Campylobacter strains tested by the cytodot procedure.

DETAILED DESCRIPTION OF THE INVENTION AND BEST MODE

The first step taken in the development of the probes of the present invention involved identification of regions of 16S rRNA which could potentially serve as target sites for Campylobacter specific nucleic acid probes. As a practical matter, it is difficult to predict, a priori, which non-Campylobacter organisms might be present in any test sample. Because of the large number of such potential non-Campylobacter bacteria, demonstrating adequate exclusivity for any given probe is extremely difficult and laborious and of unpredictable outcome. A more rigorous criterion was adopted to obviate the need to Know, during initial stages of research and development, what non-Campylobacter bacteria might be present in all test samples that ultimately will be screened using the probe. This entailed knowledge of the phylogenetic relationships among Campylobacter and between Campylobacter and other groups of bacteria. Specifically, an operating but previously unproven hypothesis was adopted that the exclusivity criterion could be satisfied by determining that if a particular target region in Campylobacter rRNA, sufficiently different from the homologous region in the rRNA of representative yet close evolutionary relatives of Campylobacter, could be identified, then a probe to such a sequence could be used to distinguish between the Campylobacter and the relatives by hybridization assay. Based on phylogenetic observations, it was then extrapolated that rRNA sequences of more distantly related organisms, even though their actual identity may not necessarily be known, should be predictably different in a particular region of sequence than the aforementioned close evolutionary relatives of Campylobacter. However, it cannot be predicted, a priori, whether such regions exist or, if they do, where within the rRNA such regions will be located.

As our first step in identifying regions of Campylobacter rRNA which could potentially serve as useful target sites for nucleic acid hybridization probes, nearly complete nucleotide sequences of the 16S rRNAs from a number of Campylobacter species were determined (see Table 2). These were selected as representative of the evolutionary breadth of the genus Campylobacter. The nucleotide sequences of various portions of the rRNAs were determined by standard laboratory protocols either by cloning (Maniatis et al., 1982, Molecular Cloning: A Laboratory Manual, Cold Spring Harbor Laboratory, New York, 545pp) and sequencing (Maxam & Gilbert, 1977, Proceedings of the National Academy of Science, USA 74:560–564; Sanger et al., 1977, Proceedings of the National Academy of Science, USA 74:5463–5467) the genes which specify the rRNAs, and/or by direct sequencing of the rRNAs themselves using reverse transcriptase (Lane et al., 1985, Proceedings of the National Academy of Science, USA 82:6955–6959).

The nucleotide sequences so obtained were compared to one another and to other available rRNA nucleotide sequences, in particular to those derived from the bacteria shown in Table 1. The preferred regions of sequence shown in Table 2 were identified as potentially exhibiting useful inclusivity and exclusivity characteristics with respect to these species.

Further experimental testing of each nucleic acid probe was conducted in order to rigorously demonstrate whether the desired characteristics discussed above could indeed be obtained, namely: 1) adequate exclusivity to all, even closely related, non-Campylobacter organisms, 2) useful inclusivity patterns with respect to Campylobacter strains, and 3) accessibility of the target regions under various assay conditions that might actually be employed. Because of the extremely large number of organisms potentially relevant to defining exclusivity (particularly in stool samples where a very large variety and abundance of non-Campylobacter bacteria are found) and inclusivity (on the order of 15 species and biogroups of Campylobacter, and a larger number of "Campylobacter-like organisms") characteristics of test probes, an iterative strategy was adopted to test and refine potential probes. In addition to test panels of cultured organisms, some 75 Campylobacter culture-negative stool specimens were screened using the probes in order to more rigorously demonstrate appropriate exclusivity behavior (Example 1—Specific). The probes were conveniently synthesized by standard phosphoramidite techniques (Caruthers, M. H. et al. [1983], in Gene Amplification and Analysis, eds. Papas, T. S., Rosenberg, M., Charikjian, J. G., Pub. Elsevier, New York, Vol. 3 pp.1–26) on an Applied Biosystems instrument.

"Dot blot" analysis, in accordance with well known procedures, was employed to preliminarily test the inclusivity and exclusivity properties of these first generation probes. As is known, dot blot analysis generally involves immobilizing a nucleic acid or a population of nucleic acids on a filter such as nitrocellulose, nylon, or other derivatized membrane which can be readily obtained commercially, specifically for this purpose. Either DNA or RNA can be easily immobilized on such a filter and subsequently can be probed or tested for hybridization under any of a variety of nucleic acid hybridization conditions (i.e. stringencies) with nucleic acid probes of interest. Under stringent conditions, probes whose nucleotide sequences have greater complementarity to the target sequence will exhibit a higher level of hybridization than probes containing less complementarity. For the oligonucleotide probes described herein, (i.e., 30–36 nucleotides) hybridization to rRNA targets at 60° C., for 14–16 hours (in a hybridization solution containing 0.9M NaCl, 0.12M Tris-HCl, pH 7.8, 6 mM EDTA, 0.1M $KPO_4$, 0.1% SDS, 0.1% pyrophosphate, 0.002% Ficoll, 0.02% BSA, and 0.002% polyvinylpyrrolidine) followed by three, 15 minute post-hybridization washes at 60° C. to remove unbound probes (in a solution containing 0.03M NaCl, 0.004M Tris-HCl, pH 7.8, 0.2 mM EDTA and 0.1% SDS), would be sufficiently stringent to produce the levels of specificity and sensitivity demonstrated in the tables and examples. Techniques are also available in which DNA or RNA present in crude (unpurified) cell lysates can be immobilized without having to first purify the nucleic acid in question (referred to herein as cytodots, see for example Maniatis, T., Fritsch, E. F. and Sambrook, J. (1982) Molecular Cloning, a Laboratory Manual). This latter approach significantly decreases the amount of effort required to screen for particular nucleotide sequences which may be present in the nucleic acids of any particular organism and, moreover, is advantageously amenable to the mass screening of large numbers of organisms. Therefore, it is the method of choice for exclusivity and inclusivity screening of potential nucleic acid hybridization probes versus large numbers of organisms.

A list of non-Campylobacter bacteria which exemplify the type of bacteria that may be present in potentially Campylobacter containing samples is given in Example 4. As discussed above, a probe which demonstrates good exclusivity characteristics to such a broad representation of bacteria can reasonably be predicted to behave similarly to a much broader list of more distantly related enteric organisms. This prediction is borne out by the data shown in Example 1—Specific in which the preferred probes (using a preferred assay format) did not cross-react with any of the non-Campylobacter bacteria present in 75 out of 75 Campylobacter culture-negative stool specimens tested.

Several other considerations also affect optimal design characteristics of a probe. The first is consideration of the geometry of the probe with respect to itself (i.e., intramolecular interactions). It has been discovered that potentially useful target sequences of 16S and 23S rRNAs most often are located in regions that exhibit a substantial possibility for self-complementarity. As a result, probes to these regions must be long enough and of appropriate geometry to compete with the secondary structure of the target molecule itself. Secondly, probes to such (structured) target regions can also exhibit self-complementarity. Because potential interactions between the probe and target sequences are governed by the same types of parameters that govern the intramolecular annealing of the target or probe sequences to themselves, it is possible, particularly under solution hybridization conditions, that self-complementary probes can render themselves inaccessible for hybridization to their target sequences. Thus, one important aspect of the probe design is to minimize such self-complementarity. This necessitates making a compromise between maximum utilization of Campylobacter-specific sequences and acceptable probe geometry.

A second consideration in probe design arises with respect to the inclusivity criterion. The preferred probe will be one which, while displaying appropriate exclusivity behavior, can also hybridize to the rRNA(s) of all desired Campylobacter bacteria. Because the genus Campylobacter itself is comprised of bacteria which exhibit significant phenotypic and genotypic (including, as disclosed below, rRNA) diversity, the design of such an "ideal" probe is greatly complicated. In practice, rather than searching for a single "universal" Campylobacter probe, a set of Campylobacter-specific probes is more preferably sought, each of which exhibits appropriate exclusivity along with a useful level of inclusivity. In aggregate, a preferred set of probes should ideally detect most or all Campylobacter and no non-Campylobacter bacteria. In such a set, for example, one probe may detect all but one or a few important Campylobacter strains, and another probe may hybridize only to those few Campylobacter strains missed by the first probe. Thus, although the probes disclosed below are characterized on an individual basis with respect to inclusivity characteristics, it should be recognized that the concept of "sets" of specific probes as detailed above is preferably considered in determining the importance of individual probes and in constructing assay kits.

The final steps of probe design and analysis ideally comprise testing actual (e.g., food/clinical/environmental) samples and then selecting suitable probes for a final probe set so that the desirable properties are optimized under real assay conditions.

Probes

The foregoing probe selection strategy yielded a number of probes useful for identifying Campylobacter bacteria in samples. As outlined in the Brief Description, Table 2 gives the probe sequences, aligned upon their target sites in the rRNAs of representative Campylobacter strains; Tables 2A through 2D detail the preferred probes.

Table 3 shows the hybridization behavior of the probes versus "cytoblots" of various Campylobacter and non-Campylobacter bacteria. In this experiment the probes were radioactively labelled with Phosphorous-32 for detection and quantitation. Hybridization conditions comprised hybridizing at 60° C. for 14–16 hours in the hybridization solution previously described.

It will be readily recognized, however, that as assay formats of higher stringency are employed, the use of longer versions of the probes may become more desirable in order to maintain an equivalent level of sensitivity (hybridization efficiency).

Table 2A describes four probes, targeted at the 124 to 225 region of Campylobacter 16S rRNA (using the E. coli position numbering). The probes designated 345 and 346 have also been identified under the nomenclature AR197 and AR196, respectively. Both were demonstrated to hybridize specifically to rRNA from members of the genus Campylobacter. Under certain sensitive assay formats, probes 345 and 346 can exhibit some undesirable cross-hybridization to some non-Campylobacter present in normal stool specimens, and accordingly these probes are less preferred. Based upon additional sequence analysis, probes 999 and 732 were designed and tested. These are shorter than their "parent" probes (31 and 35 nucleotides long, respectively, versus 50 for both 345 and 346); they also utilize different portions of the Campylobacter-specific sequence positions located in 16S rRNA region 124–225, and thus bear a somewhat different relationship to the thermodynamically favored secondary structure of this target region than probes 345 and 346. Overall, probes 999 and 732 advantageously exhibit equivalent (i.e., full) inclusivity for the target species of Campylobacter (C. jejuni, C. coli and C. laridis) and improved exclusivity with respect to that shown by probes 345 and 346. Significantly less hybridization to non-C. jejuni, C. coli and Campylobacter laridis is exhibited by probes 999 and 732, but this is deemed an acceptable compromise given the improved exclusivity in the presently preferred assay formats (and also because of the relative incidence of various Campylobacter species in stool—C. jejuni>C. coli>C. laridis>>>all other Campylobacter, as discussed above).

Probes 732 and 999 are, therefore, the most preferred probes described herein because of the lust described inclusivity and exclusivity behavior and also because of their apparent sensitivity. The hybridization behavior of probes 732 and 999 is detailed in Table 3 and Examples 1–4. Table 3 shows the behavior of the probes individually in a cytodot format. Examples 1–4 detail the hybridization behavior of the probes used in combination in a most preferred, dual-specific, liquid hybridization format.

Note that in the dual-specific assay format (described in detail below—Example 1), hybridization of both probes is required to produce a positive result. Therefore, the effect of undesirable hybridization (i.e., to non-Campylobacter) by either probe alone may be significantly reduced, if not abolished, in this format.

Table 2B describes two probes, designated 1104 and 1105, targeted at the 391 and 501 region of Campylobacter 16S rRNA (using the E. Coli position numbering). Probe 1104 hybridizes to all C. jejuni (5), C. coli (3), and C. laridis (5), which have so far been tested and, in addition, hybridizes to 58 of 62 partially characterized, clinical isolates (mostly C. jejuni). It also hybridizes to a number of, but not all other Campylobacter species. Of the non-Campylobacter tested, only W. curva is detected to any significant extent by probe 1104. Probe 1105 hybridizes to all Campylobacter strains and species so far tested. It also hybridizes to the Bacteroides and Wolinella strains shown in Tables 1 and 2, but not to the enteric strains, E. coli, S. typhimurium, etc. The hybridization behavior of probe 1105 or derivatives thereof would potentially make it a most useful "broad-specificity" probe for the identification/detection of the entire group of Campylobacter and "relatives" shown in Table 1. It is of note that this entire grouping is, by a variety of genetic and biochemical criteria, quite distinct from all other bacteria. A probe or probe set useful for detecting the presence of any member of the group in a natural (e.g. clinical, food or environmental, sample would be potentially valuable research tool for studying the occurrence and epidemiology of these still poorly understood bacteria. Since many of the non-C. jejuni, C. coli and Campylobacter laridis are very difficult to isolate or cultivate, not much really is known about their prevalence in the environment or about their association with disease states in animals and humans. These probes would serve as useful tools in gaining such understanding.

Table 2C describes three probes, designated 1130, 1132 and 1133 which are targeted at the 973 to 1049 region of Campylobacter 16S rRNA (using the E. coli position numbering). All exhibit full inclusivity for the C. jejuni, C. coli and C. laridis strains tested (Table 3) and, in addition, detect all 62 of the clinical isolates. Limited hybridization to a small number of non-jejuni, coil or laridis Campylobacter strains is exhibited by all three probes to this region under the hybridization conditions employed. All show excellent exclusivity behavior and likely will be extremely useful as Campylobacter-specific probes.

Note that probes 1132 and 1133 differ only at one position. This difference reflects the heterogeneity observed among the target Campylobacter at this position.

Analog-C, first mentioned in the legend of Table 2C, is 2'-deoxycytidine which has been modified at the C-4 position with a 1,3-propane diamine side chain (Schulman, L. H. et al. (1981), Nucl. Acids Res. 9, 1203–1217). This compound is converted to a phosphoramidite which can be incorporated into a DNA probe using the solid phase synthetic methods developed by Caruthers (Caruthers, M. H., et al. (1982), in Genetic Engineering, Setlow, A. and Hollaender, J. K. (eds.), Vol. 4, pp 1–17, Plenum Press, New York). This primary amine then can be selectively derivatized with, for example, a biotin or fluorescein ligand which can be used to detect the synthetic oligonucleotide (Rashtchian, A., et al., 1987, Clin. Chem. 33/9, 1526–1530).

Table 2D describes two probes including 351, previously disclosed as Probe AR351. The other, probe 1134, was derived from, and is shorter then probe 351 but makes use of the same novel structural element in Campylobacter 16S rRNA. Both 351 and 1134 are targeted at the 1424–1489 region of Campylobacter 16S rRNA. Note in Table 2D that, near the middle of the target sequences for probes 351 and 1134, the Campylobacter rRNAs have a conserved deletion of six nucleotides with respect to the E. coli sequence in this region. The E. coli structure is much more representative of that exhibited by the vast majority of eubacteria and thus renders probe 1134 quite specific for Campylobacter. Additional nucleotide differences vicinal to this deletion among the Campylobacter and between the Campylobacter and Bacteroides, Wolinella, etc., further serve to restrict the hybridization of probes 1134 and 351 to members of the C. jejuni, C. coli and C. laridis group of Campylobacter. While some limited hybridization to a few other Campylobacter is detected on dot blots (Table 3), no hybridization to non-Campylobacter is detectable.

EXAMPLE 1

General

A Homopolymer Capture, Dual Probe, Liquid Hybridization Format

Cultures containing Campylobacter and/or non-Campylobacter bacteria are grown in appropriate broth, then the nucleic acids are released by any of a number of appropriate lysis agents (e.g., NaOH, guanidine salts, detergent, enzymatic treatment, or some combination of the aforementioned). Hybridization is carried out with two different probes or probe sets at least one of which, but not necessarily both, must be specific for the organism to be detected. In this example, the Campylobacter specific "capture" probe 732 is enzymatically tailed with 20–200 deoxyadenosine (dA) residues at its 3'-terminus, and the reporter probe, 999, is labeled either chemically or enzymatically with radioactive phosphorus (P-32) or other small ligand (e.g., fluorescein or biotin, the former being used in this experiment) which is used to detect the captured target molecules.

Generally, following cultivation/enrichment, bacteria present in the test samples are transferred in small aliquots to test tubes. The bacteria are lysed, the capture and detection probes are added, and hybridization is allowed to proceed in an appropriate solution at an appropriate temperature such as described below (Example 1—Specific). The solution containing the target/probe complex then is brought into contact with a surface containing bound deoxythymidine (dT) homopolymer 15–3000 nucleotides in length, under conditions that will allow hybridization between the dA and dT. In this example, the dT is bound to a plastic "dipstick" which is submerged in the target/probe solution. If Campylobacter ribosomal RNA was present in the test sample, the dA tailed, Campylobacter-specific capture probes would have hybridized to the target rRNA sequences present and, in turn, would be captured onto the dipstick. Unhybridized nucleic acids and cellular debris are washed away a described below, leaving the captured DNA-RNA complex attached to the surface via the dA-dT duplex. The reporter probe also is bound to the dipstick via the chain of interactions—Capture surface-dT: dA-Capture probe: Target:Reporter Probe—only if the correct target nucleic acid is present. The bound, ligand derivatized (e.g., fluoresceinated) reporter probe then is detected by the addition of a ligand binding-enzyme complex (e.g., horseradish peroxidase-conjugated anti-fluorescein antibody, in this example). Following incubation under conditions permitting specific binding of the detection complex, washing to remove non-bound enzyme, addition of chromogenic substrate and subsequent color development (typically 20–30 minutes), and the optional addition of color-termination solution, the developed color is measured colorimetrically. This reading (typically in the range of 0.1>2.0 Absorbance units) is compared to the negative control levels, a threshold or cutoff value is established, and a determination of the "significance" of the experimental levels is made.

EXAMPLE 1

Specific

For clinical stool specimens, 1 g of the sample was added to 3 ml of Campylobacter stool processing buffer (3.25M guanidine thiocyanate, 0.4M Tris-HCl (7.5), 0.08M EDTA, 13% dextran sulfate 5000, 0.325% sarkosyl) and vortexed until the sample was homogenized.

0.70 ml of the processed sample was used for each hybridization. The nucleic acid released from each sample was detected by addition of 0.05 ml specific capture and detector probes (containing 1.0 microgram/ml of preferred capture probe 732 and 0.5 microgram/ml of detector probe 999-FITC). A capture dipstick was placed into each test tube (containing bacterial lysate and the specific probes). The contents were incubated in a 37° C. water bath for 60 minutes to enable hybridization of specific capture and reporter probes to target nucleic acids and the capture of these specific DNA/rRNA hybrids to the dipsticks as described above.

After hybridization, the dipsticks were washed by briefly submerging the dipsticks in a wash basin containing enough wash solution to cover the active dT coated part of the dipstick (50 mM Tris, pH 7.5, 150 mM NaCl, 2 mM EDTA, and 0.1% Tween 20, room temperature) for one minute.

The washed dipsticks were removed from the wash basin, blotted dry with absorbent paper, placed into a set of test tubes containing 0.75 ml antibody-enzyme conjugates (anti-fluorescein-horseradish peroxidase diluted in wash buffer), and allowed to incubate at room temperature for 20 minutes.

After allowing the antigen-antibody reaction to occur, the dipsticks were removed from the test tubes, washed and blotted in the same manner as described in the preceding two paragraphs. The dipsticks were placed into a set of labeled test tubes containing substrate-chromogen mixtures (urea-peroxide:tetramethyl benzidine [Ventrex, Portland, Maine], 2:1) and allowed to incubate at room temperature for 20 minutes. The dipsticks were then removed and the color development step terminated by the addition of 0.25 ml 4N sulfuric acid. The absorbance of the samples was measured colorimetrically using light of wave length 450 nanometers.

Sample tubes with <0.1 O.D. values were considered positive for Campylobacter, those with lower absorbance values indicated the absence of Campylobacter. Results from 148 stool specimens tested as above are shown below:

|  | CULTURE | |
| --- | --- | --- |
|  | Positive | Negative |
| Invention Assay | (Confirmed +) | (False +) |
| Positive | 71 | 0 |
| Negative | (False −) 2 | (Confirmed −) 75 |

$$\text{Sensitivity} \equiv \frac{\text{(Confirmed+)}}{\text{(Total Culture+)}} \times 100 = \frac{71}{71+2} \times 100 = 97\%$$

$$\text{Specificity} \equiv \frac{\text{(Confirmed−)}}{\text{(Total Culture−)}} \times 100 = \frac{75}{75+0} \times 100 = 100\%$$

(≡ means "defined as")

EXAMPLE 2

The above procedures were repeated on negative pooled stools which had been seeded with different concentration of *Campylobacter jejuni*. The following results were obtained:

| Seeded Concentration CFU/ml | Absorbance 450 nm |
| --- | --- |
| 0 | 0.01 |
| $1 \times 10^4$ | 0.13 |
| $1 \times 10^5$ | 0.38 |
| $1 \times 10^6$ | 0.73 |
| $1 \times 10^7$ | 1.50 |

While the description of the invention has been made with reference to detecting rRNA, it will be readily understood that the probes described herein and probes complementary to those described herein will also be useful to detect the genes (DNA) encoding the rRNA and accordingly, such probes are to be deemed equivalents to the described probes and encompassed within the spirit and scope of the present invention and the appended claims.

EXAMPLE 3

Following the procedures of Example 1, Campylobacter isolates were "seeded" into negative pooled stool at $10^7$ CFU/ml and tested in the preferred liquid format using capture probe 732 and detector probe 999-FITC, Sources for the listed bacterial strains are as given in Table 3. The results obtained were:

| ORGANISM | STRAIN | ABSORBANCE 450 NM |
| --- | --- | --- |
| C. JEJUNI | 33560 | 1.03 |
| C. JEJUNI | N933 | 0.99 |
| C. JEJUNI | 29428 | 0.90 |
| C. LARIDIS | UA487 | 1.05 |
| C. LARIDIS | UA577 | 1.04 |
| C. LARIDIS | 35223 | 0.89 |
| C. COLI | 33559 | 0.88 |
| C. COLI | 84-29 | 0.83 |
| C. FETUS FETUS | 33246 | 0.12 |
| C. FETUS VENEREALIS | 33561 | 0.08 |
| C. HYOINTESTINALIS | 35217 | 0.10 |
| C. MUCOSALIS | 43264 | 0.09 |
| C. SPUTORUM | 33562 | 0.14 |
| C. CRYAEROPHILIA | 43157 | 0.06 |
| C. PYLORI | 43504 | 0.03 |

EXAMPLE 4

Example 3 was repeated except that non-Campylobacter isolates were "seeded" into negative pooled stool at $10^8$ CFU/ml and tested in the preferred liquid format using capture probe 732 and detector probe 999-FITC, Sources for the listed bacterial strains are as given in Table 3; in addition: (6) Silliker Laboratories, Chicago, Ill., The observed results were as follows:

| ORGANISM | STRAIN | SOURCE | ABSORBANCE 450 NM |
| --- | --- | --- | --- |
| ACINETOBACTER CALCOACETICUS | 19606 | (1) | 0.01 |
| AEROMONAS HYDROPHILIA | 7965 | (1) | 0.01 |
| ALCALIGENES FAECALIS | 8750 | (1) | 0.01 |
| BACILLUS CEREUS | 14579 | (1) | 0.00 |
| BACTEROIDES FRAGILIS | 23745 | (1) | 0.01 |
| BACTEROIDES GRACILIS | 33236 | (1) | 0.01 |
| BACTEROIDES MELLANINOGENICUS | 25845 | (1) | 0.02 |
| BACTEROIDES THETAIOTAMICRON | 27941 | (1) | 0.03 |
| BACTEROIDES UREOLYTICUS | 33387 | (1) | 0.01 |
| BIFIDOBACTERIUM BIFIDUM | 35914 | (1) | 0.00 |
| CANDIDA ALBICANS | 18804 | (1) | 0.03 |
| CANDIDA GLABRATA | 2001 | (1) | 0.03 |
| CANDIDA STELLATOIDIAE | 36232 | (1) | 0.00 |
| CANDIDA TROPICALIS | 750 | (1) | 0.00 |
| CITROBACTER DIVERSUS | 27156 | (1) | 0.00 |
| CITROBACTER FREUNDII | S135 | (6) | 0.00 |

| ORGANISM | STRAIN | SOURCE | ABSORBANCE 450 NM |
|---|---|---|---|
| CLOSTRIDIUM DIFFICILE | 9689 | (1) | 0.01 |
| CLOSTRIDIUM PERFRINGENS | 3624 | (1) | 0.01 |
| CLOSTRIDIUM SORDELLII | 9714 | (1) | 0.01 |
| EDWARDSIELLA TARDA | 15947 | (1) | 0.02 |
| ENTEROBACTER AEROGENES | 13048 | (1) | 0.01 |
| ENTEROBACTER AGGLOMERANS | S121 B | (6) | 0.01 |
| ENTEROBACTER CLOACAE | S134 | (6) | 0.03 |
| ESCHERICHIA COLI | 12036 | (1) | 0.01 |
| FUSOBACTERIUM MORTIFERUM | 9817 | (1) | 0.01 |
| HAFNIA ALVEI | 29927 | (1) | 0.01 |
| KLEBSIELLA OXYTOCA | 13182 | (1) | 0.01 |
| KLEBSIELLA PNEUMONIAE | S122 F | (6) | 0.02 |
| MORGANELLA MORGANII | 25830 | (1) | 0.00 |
| NEISSERIA GONORRHOEAE | 9793 | (1) | 0.00 |
| PEPTOCOCCUS ASACCHAROLYTICUS | 29743 | (1) | 0.00 |
| PEPTOCOCCUS MAGNUS | 29328 | (1) | 0.03 |
| PEPTOSTREPTOCOCCUS ANAEROBIUS | 27337 | (1) | 0.00 |
| PLESIOMONAS SHIGELLOIDES | 14029 | (1) | 0.00 |
| PROPIONIBACTERIUM ACNES | 6919 | (1) | 0.03 |
| PROTEUS MIRABILIS | IG 3109 | (5) | 0.01 |
| PROTEUS VULGARIS | 13315 | (1) | 0.01 |
| PROVIDENCIA ALCALIFICIENS | 9886 | (1) | 0.01 |
| PROVIDENCIA RETTGERI | 29944 | (1) | 0.00 |
| PROVIDENCIA STUARTII | 29914 | (1) | 0.04 |
| PSEUDOMONAS AERUGINOSA | IG 928 | (5) | 0.00 |
| SALMONELLA TYPHIMURIUM | 23566 | (1) | 0.00 |
| SERRATIA MARCESENS | RF 972 | (1) | 0.01 |
| SHIGELLA DYSENTERIAE | RF 970 | (1) | 0.00 |
| STAPHYLOCOCCUS AUREUS | 12600 | (1) | 0.00 |
| STREPTOCOCCUS FAECALIS | 19433 | (1) | 0.00 |
| VIBRIO PARAHEMOLYTICUS | 17802 | (1) | 0.02 |
| WOLLINELLA CURVA | 33238 | (1) | 0.00 |
| WOLLINELLA RECTA | 35224 | (1) | 0.00 |
| WOLLINELLA SUCCINOGENES | 25943 | (1) | 0.02 |
| YERSINIA ENTEROCOLITICA | 9610 | (1) | 0.01 |

TABLE 1

16S rRNA RELATIONSHIPS AMONG THE CAMPYLOBACTER & "RELATIVES".

---

CAMPYLOBACTER *JEJUNI*
CAMPYLOBACTER COLI
CAMPYLOBACTER *LARIDIS*

---

CAMPYLOBACTER *FETUS*
CAMPYLOBACTER *HYOINTESTINALIS*

WOLINELLA RECTA
WOLINELLA CURVA
BACTEROIDES GRACILIS
BACTEROIDES UREOLYTICUS

CAMPYLOBACTER *SPUTORUM*

---

CAMPYLOBACTER *CRYAEROPHILA*

CAMPYLOBACTER *NITROFIGILIS*

---

CAMPYLOBACTER *CINAEDI*
CAMPYLOBACTER *FENNELLIAE*
FLEXISPIRA RAPPINI

THIOVULUM
WOLINELLA SUCCINOGENES

CAMPYLOBACTER *PYLORI*

TABLE 2A

CAMPYLOBACTER 16S rRNA PROBE TARGET SITE 124 TO 225.

| Position # | 124 | | 225 |
|---|---|---|---|
| E. coli | CUGGG--AAACUGCCUGAUGGAGGGGGAUAACUACUGGAAACGGUAGCUAAUACCGCAUAACGUC | ————GCAA————GACCAAAGAGGGGGACCUUCGGCCUCUGCCAUC | |
| C. jejuni 1 | AUAGUUAAUCUGCCCUACACAAGAGGACAACAGUUGGAAACGACUGCUAAUACUCCUGCUUAACACAAGUUGAGUAGGGAAAG | ————UUUUU————CGGUGUA | |
| C. jejuni 2 | AUAGUUAAUCUGCCCUACACAAGAGGACAACAGUUGGAAACGACUGCUAAUACUCUCUGCUUAACACAAGUUGAGUAGGGAAAG | ————UUUUU————CGGUGUA | |
| C. jejuni 3 | AUAGUUAAUCUGCCCUACACAAGAGGACAACAGUUGGAAACGACUGCNNAUACUCUCUGCUUAUAUCCUGCUUAACACAAGUUGAGUAGGGAAAG | ————UUUUU————CGGUGUA | |
| C. coli | AUAGUUAAUCUGCCCUACACAAGAGGACAACAGUUGGAAACGACUGCUHAUACUCUAUAUCCUGCUUAACACAAGUUGAGUAGGAHAG | ————UUUUU————CGGUGUA | |
| C. laridis | AUAGUUAAUCUGCCCUACACAAGAGGACAACAGUUGGAAACGACUGCUUAAUACUCUAUACUCCUGCUUAACAYAAGUUGACUAGGGAAAG | ————UUUUU————CGGUGUA | |
| Probe 345 | | GAGAUAUGAGGACGAAUUGUGUUCAACUUCAUCCCUUUC————AAAAA————GCCACAU | |
| Probe 346 | TCAAUUAGACGGGAUGUGUUCUCCUGUUGUCAACCUUUGCUGACGAUUAU | | |
| Probe 999 | | GACGAUUAUGAGAUAUGAGGACGAAUUGUGU | |
| Probe 732 | CAAUUAGACGGGAUGUGUUCUCCUGUUGUCAACCU | | |
| C. fetus f | AUAGUUAAUCUGCCCUACACAGGAGGACAACAGUUAGAAAUGACUGCUMAUACUCCCUUCUUAACAUAAGUUAAGUCGGGAAAG | ————UUUUU————CGGUGUA | |
| C. hyoint | AUAGUUAAUCUGCCCUACACUGGAGGACAACAGUUAGAAAUGACUGCUAAUaCUCCAUWCUCCUUCUUAACAUAAGUUAAGUUGGGAAAG | ————CCCUUU————CGGUGUA | |
| C. cryaero | AUAGGUAAAUAUGCCUCUCUUACUAAGGGAAACAAUUGGAAACGAUUGCAAAUGACUGCUAAUACUCCUUAUAUAAGGGAAAGA | ————UUUA————UUGGUAAG | |
| Thiovulum | AUAGnUUUACAUGCCUnUCGGUCGGGACAACAGUUGGAAAACGACUGCUAAUACCCGAUAUUCCA | ————GAAA————UGGGAAAG————CGCCGAA | |
| W. succino | AUAGGUUAUGUGUGCCCAUAGUCGGAAUAGCCACUGGAAAUAGCCGUGAUUAAAUACCGGAUAUUCCC | ————GAGA————GGGGAAAG————CGCUAUG | |
| F. rappini | AUAGGUUAUGUGCCCUUUAGUCGGAUAGCCACUGGAAAACGGCGAUAGGAUUAAAUACUGGAUNNCUUC | ————UACG————GGGGAAAGG————UCGCUAAA | |
| C. pylori | AUAGGUCAUGUGCCUCUUAGUUUGGGAUAGCCAUGAUGGAAAACGAUGAUUAAAUACCAGAUnUCCC | ————UACG————GGGGAAAGA————UUUA————UCGCUAAG | |

Legend. 16S rRNA sequences are written in the 5' to 3' direction. Probe sequences are written as DNA, in the 3' to 5' direction. 16S rRNA sequences are aligned with respect to the E. coli sequence which is used as a reference for identifying the Probe Target region. Numbers above the E. coli sequences refer to the number of nucleotide residues counting from the 5' end of the E. coli 16S rRNA sequence. C, A, G, U represent the ribonucleotide bases Cytosine, Adenosine, Guanosine, and Uridine, respectively. W, Y, M, H and N represent uncertain nucleotide assignments: W = A or U, Y = C or U, M = C or A, H = A, C or U, N = A, C, G or U. Lower case letters in the RNA sequences indicate uncertainty in the existence of a nucleotide at that portion. Dashes are alignment gaps indicating that no nucleotide is present at that position in the sequence where it appears. Probe 345 is equivalent to probe AR197 and probe 346 is equivalent to probe AR196 as described in application SN821,393. E. coli = Escherichia coli sequence from GenBank Data Base; C. jejuni = Campylobacter jejuni strain N941, clinical isolate from Gary Doern, Univ. of Massachusetts Medical Center, Worcester, MA; C. jejuni 2 and C. jejuni 3 are, respectively, strains 2942B and 33560, supplied by the American Type Culture Collection (ATCC); C. coli = Campylobacter coli strain ATCC33559; C. laridis = Campylobacter laridis ATCC35223; C. fetus f = Campylobacter fetus subspecies fetus strain 5396 (Collection of the Institut Pasteur, Paris, France), sequence from P. Romaniuk, pers. comm.; C. hyoint = Campylobacter hyointestinalis ATCC35217; C. cryaero = Campylobacter cryaerophila ATCC43157; Thiovulum cells were isolated from enrichment cultures by D. Stahl (as described in Stahl et al., 1987, Intn'l J. System. Bacteriol. 37:116-122) and sequenced by D. Stahl and D. Lane (reported in Romaniuk et al., 1987, J. Bacteriol. 169:2137-2141); W. succino = Wollinella succinogenes (sequence from Lau et al., 1987, System. & Appl. Microbiol. 9:231-238; F. rappini = Flexispira rappini strain 1937-38264, cells provided by J. Bryner, National Animal Disease Center, Ames, IA; C. pylori = Campylobacter pylori ATCC43504.

TABLE 2B

CAMPYLOBACTER 16S rRNA PROBE TARGET SITE 391 TO 501.

| | 391 | | 501 |
|---|---|---|---|
| E. coli | GCAGCCAUGCCGCGUGUAUGAAGAAGGCCUUCGGGUUGUAAAGUACUUUCAGCGGGGAG-GAAGGGAGUAAAGUUAAUACCUUUGCUCAUUGACGUUACCCGCAGAAG-AAGC | | |
| C. jejuni 1 | GCAGCAACGCCGCGUGAGGAUGACACUUUUCGGAGCGUAAACUCCUUUUCUUAGGGAA------------UCUGACGGUACCUAAGGAAU-AAGC | | |
| C. jejuni 4 | GCAGCAACGCCGCGUGAGGAUGACACUUUUCGGAGCGUAAACUCCuUUUCUUAGGGAA------------UCUGACGGUACCUnAGGAAU-AAGC | | |
| C. jujuni 5 | GCAGCNACGCCGCGUGAGGAUGACACUUUUCGGAGCGCAGCG-AAACUNCUUUUCUUAGGGAA------------UCUNNNGGUACCUAAGGAAU-AAGC | | |
| C. jejuni 6 | GCAGCNACGCCGCGUGAGGAUGAUNACACUUUUNGGAGCGUAAACUCCNUUUCUUAGGGAA------------UCUNNNGGUACCUNAGGAAU-NA.... | | |
| C. coli | GCAGCAACGCCGCGUGAGGAUGACGAUGACACUUUUCGGAGCGUAAACUCCUUUUCUUAGGGAA------------UCUGACGGUACCUAAGGAAU-AAGC | | |
| C. coli 2 | GCAGCNACGCCGCGUGAGGAUGACNCUUUUCGGAGCGUAAACUCCUUUUCUUAGGGAA------------UCUGANGGUACCUNAGGAAU-AAGC | | |
| C. laridis | GCAGCAACGCCGCGUGAGGAUGACACUUUUCGGAGCGUAAACYCCYUUUCUUUAGGGAA------------UCUGACGGUACCUAAGGAAU-AAGC | | |
| C. laridis 2 | GCAGCAACGCCGCGUGAGGAUGACACUUUUCGGAGCGUAAACUCNUUUUCUUAGGGAA------------UCUGNNGGUACCUNAGGAAU-AAGC | | |
| probe 1104 | | TcTGCGGGCGCACCUCCUACUGUGAAAAGCCUCGCAUUGAGGAAAAGc | |
| probe 1105 | | | AGACUGCCAUGGAUUCCUU-TTc |
| C. fetus 1 | GCAGCAACGCCGCGUGAGGAUGAUGACACUUUUCGGAGCGUAAACUCCNUUGUUAGGGAA------------CAUGACGGUACCUAACGAAU-AAGC |
| C. fetus 2 | GCAGCAACGCCGCGUGAGGAUGAUGACACUUUUCGGAGCGUAAACUMCNUUGUUAGGGAA------------CAUGACGGUACCUMASGAAU-AAGC |
| C. hyoint | GCAGCAACGCCGCGUGAGGAUGAUGACACUUUUCGGAGCGUAAACUCNUUGUUGGGAA------------CAUGACGGUACCAACGAAU-AAGC |
| C. concisus | GCAGCAACGCCGCGUGAGGANGAUGACACUUUUCGGAGCGUAAACUCCNUUGUWAGGGAA------------NAUGNCGGUACCUNACGAAU-AAGC |
| W. curva | GCAGCAACGCCGCGUGAGGAUGACNCUUUCGGAGCGUAAACUCUNUUUCUNGGCGAA------------UUUGACGGUNCCNAGGAAU-AAGC |
| W. recta | GCAGCANCGCCGCGUGAGGAUGAGCGNAAACUCUNNNNGGAAAGAAU------------NNUGACGGUACCCAAGGAAU-AAGC |
| B. gracilia | GCAGCAACGCCGCGUGAGGAUGAUGACACUUUUCGGAGCGUNAACUCNNNNUUGUUAGGGAA------------AAUGACGGUACCUAAGGAAU-AAGC |
| B. ureolyt | GCAGCAACGCCGCGUGAGGAUGAUGACACUUUUCGGAGCGUNAACUCCUUUUAUCAGGAAA------------AAUGACGGUACCUNAUGAAU-AAGC |
| C. sputorum 1 | GCAGCAACGCCGCGUGAGGAUGACACUUUUCGGAGCGUAAACNCCNNUUCUUUUGGGAA------------AAUGACGGUACCAAAGGAAU-AAGC |
| C. sputorum 2 | GCANCAACGCCGCGUGAGGAUGACACUUUUCGGAGCGUAAACUCCNYUUCUUUGGGAA------------AAUGACGGUACSAAAGGAAU-AAGC |
| C. cryaero | GCAGCAACGCCGCGUGGAGGAUGACAUUCGGUGCGUNAACUCCYUUUAUAUGAGAA-GAUA------------AUGACGUAUAUGAGAA-AAGC |
| C. cryaero 2 | GCAGnnACGCCGCGUGGAGGGAUnACACAUUUCGUGCGUnAACUnCUnUUAUAUGAGAA-GAUA------------AUAA.... |
| C. nitrofig | GCAGCAACGCCGCGUGGAGGAUGACACAUUUCGGUGCGUAAACUnCnUUUAUAUAGGAA-GAUA------------AUGA.... |

TABLE 2B-continued

| | CAMPYLOBACTER 16S rRNA PROBE TARGET SITE 391 TO 501. |
|---|---|
| Thiovulum | GCAGCAACGCCCGCGUGGAGGAUGACGCAUUUCGCGUGUGUAAACUCCUUUUUUCGGAGAA—GaUU————————————————aUGACGCGUAUCCGAAGAAU—AAGC |
| W. succino | GCAGCAACGCCCGCGUUGGAGGAUGAAGGUCUUCGGAUUGUAAACUCCUUUUUCUAAGAGAA—GAUU————————————————AUGACGCGUAUCUUAGGAAU—AAGC |
| C. cinaedi | GCAGCAACGCCCGCGUUGGAGGAUAAAGGUnnnAGGAUUGUAAACUnnnnUGGUAAGAGAA—GAUU————————————————AUAA.... |
| C. fennell | GCAGCAACGCCCGCGUUGGAGGAUGAAGGUnnAAGGAUUGUAAACUnCnUUUGUAAGAGAA—GAUU————————————————AUAA.... |
| F. rappini | GCAGCAACGCCCGCGUUGGAGGAUGAAGGUUUUAGGAUUGUAAACUCCUUUUGUUAGAGAA—GAUU————————————————AUGACGCGUAUCUAANGAAN—AAGN |
| C. pylori | GCAGCAACGCCCGCGUUGGAGGAUGAAGGUUUUAGGAUUGUAAACUCCYUUUGUUAGAGAA—GAUA————————————————AUGACGCGUAUCUAACGAAU—AAGC |

Legend. Organisms key and sequence notation are as in Table 2a, with the following additions: *C. jejuni 5* = *Campylobacter jejuni* strain UVIC (pers. comm. from P. Romaniuk, Univ. of Brititch Columbia, Vancouver, B.C.); *C. jejuni 6* = *Campylobacter jejuni* strain NCTC11392 (P. Romaniuk); *C. coli 2* = *Campylobacter coli* strain NCTC11366 (P. Romaniuk); *C. laridis 2* = *Campylobacter laridis* ATCC35221 (an amalgam of sequences from Romaniuk et al., 1987, and Thompson et. al., 1988, by D. Lane); *C. fetus 1* = an amalgam of reverse transcription sequences from *Campylobacter fetus* subspecies fuetus strains VPI H641 (Paster & Dewhirst, 1988), ATCC27374 (Thompson et al., 1988), and CIP5396 (Romaniuk et al., 1987) by D. Lane; *C. fetus 2* = an amalgam of *Campylobacter fetus* subspecies venerialis strain ATCC19430 (Thompson et al., 1988) and an unidentified strain (P. Romaniuk, Pers. Comm.); *C. concisus* = a *Campylobacter concisus* amalgam derived from strains FCD (Forsyth Dental Center)288, FDC484 (B. Paster & F. Dewhirst, Forsyth Dental Center, Boston, MA, Pers. Comm) and strain ATCC13086 (Thompson et al., 1988); *W. curva* = *Wollinella curva* ATCC3524; *W. recta* = *Wollinella recta* ATCC3524; *B. gracilis* = *Bacteroides gracilis* ATCC33236; *B. ureolyt* = *Bacteroides ureolyticus* ATCC33387; *c. sputorumi* = an amalgam of *Campylobacter sputorum* subspecies bubulus derived from strain ATCC33562 (= *C. sputorum*, as defined in TABLE 2A) and strain ATCC33491; *C. sputorum 2* = an amalgam of *Campylobacter sputorum* subspecies sputorum derived form strains S-17 (Thompson et al., 1988 ) and Romaniuk et al., Pers. Comm.(; *C. cryaero 2* = *Campylobacter cryaerophila* ATCC11885 (Thompson et al., 1988); *C. cinaedi* = *Campyllobacter cinaedi* ATCC35683 (Thompson et al., 1988); *C. fennell* = *Campylobacter fennelliae* ATCC35684 (Thompson et al., 1988); S = C or G uncertainty in nucleotide assignment.

TABLE 2C

CAMPYLOBACTER 16S rRNA PROBE TARGET SITE 973 TO 1049.

| Position # | 973 — 1049 |
|---|---|
| E. coli | GAAGAACCUUACCUGGUCUUGACAUCCACGGAAGUUUUCAGAGAUGAGAAUGUG-CC--UUCG--GGAACCGUGAGAGACAGGU |
| C. jejuni 1 | GAAGAACCUUACCUGGGCUUGACAUAUUCCUAAGAAUCCUUWUAGAGAUAWGAGGGUG-CUAGCUUGCUAGAACUUAGAGACAGGU |
| C. jejuni 2 | GAAGAACCUUACCUGGNYUUGAUAUCCUAAGAACCUUUUAGAGAUAAGAGAUAAGAGGGUG-CUAGCUUGCUAGAACUUAGAGACAGGU |
| C. jejuni 3 | GAAGAACCUUACCUGGNNNUGAUAUCCUAAGAACCUUUUAGAGAUAAGAGAGAUAAGAGGGUG-CUAGCUUGCUAGAACUUAGAGACAGGU |
| C. coli | GAAGAACCUUACCUGGGCUUGACAUAUCCUAAGAACCUUUUAGAGAUAAGAGAGGGUG-CUAGCUUGCUAGAACUUAGAGACAGGU |
| C. laridis | GAAGAACCUUACCUGGGCUUGACAUAUCCUAAGAGAUAAGAGGGUG-CUAGCCUUGCUAGAACUUAGAGACAGGU |
| Probe 1132 | Tc CTATACTCCCAC-GATCGAACGAUCUUGAAUCUCUGC |
| Probe 1133 | Tc CTATTCTCCCAC-GATCGAACGAUCUUGAAUCUCUGc |
| Probe 1136 |  |
| Probe 1130 | Tc TCTTGGAATGGACCCGAACTATAGGATTCTTGGAAc |
| C. hyoint | GAAGAACCUUACCUGGGCUUGACAUAUCCUAAUAACACUUAGAGAUAAGAUNGUG-CUUGUUUACAAGAAAUUAGUGACAGGU |
| C. sputorum | GAAGAACCUUACCUGGGCUUGACAUAUCCUAGACUCUAGAGAUAGAAGAGUG-UCUGCUUGCAGAAAAUGUUAAGACAGGU |
| C. cryaero | GAAGAACCUUACCUGGCUKGACUUGACAUAGAACUUUCUAGAGAUAGAUAGAUUGGUG-UCUGCUUGCAGUWACUUAUAUACAGGU |
| Thiovulum | GAAAACCUUACCUUGACCCUUGACAUUGUAAGAAUUUUGCAGAGAUGAAAGUG-CU---UCG--GGAACUUGAAAACAGGU |
| W. succino | GAAGAACCUUACCUGGCuUGACAUUGAu a GAAUCCUAUAGAGAUAUAUGGGAGUG-CCAGUUUACUGGAGCUUGAa a CAGGU |
| F. rappini | GAAGAACCUUACCUAGGCUUGACAUUGAUAGAAUCCGCUAGAGAUAGAUAGUGGAGUG-CUGGCUUGCCAGAGCUUGAAAACAGGU |
| C. pylori | GAAGAACCUUACCUAGGCUUGACAUUGGAGAAUCCGCUAGAAAAUAGUGGAGUGUCUAGCCUUGCUAGACCUUGAAAACAGGU |

Legend. Organism key and sequence notation are as in Tables 2A & 2B, with the following additions: C. sputorum = Campylobacter sputorum subspecies bubulus ATCC33562. Certain of the probe oligonucleotides have a lower case C (c) at one or both ends. This designates an "analog c" residue to which various "detection" ligands (e.g. biotin, fluorescein) can be readily attached. They do not otherwise affect the behavior of the probes. In appending an analog c to the 3' ends during direct systesis, a T residue often is coupled first as a convenience in the synthesis. Again the T residue is not a necessary part if the probe "proper" in that it does not necessarily participate in the hybridization of the probe to its target sequence.

TABLE 2D

CAMPYLOBACTER 16S rRNA PROBE TARGET SITE 1424 TO 1489.

```
Position #  1424                                                                    1489
            |                                                                          |
E. coli     UUGCAAAAGAAGUAGGUAGCUUAACCUUCGGGAG-GG-CGCUUACCACUUUGUGAUUC--AUGACUGGGG C.jejuni 1  UUUCACUCGAAGCCGGAAUACUAAACU------A-GU-UACCGUCCACAGUGGAAUCACCGGCGCUGGGG C.jejuni 2  UUUCACUNGAAGCCGGAAUACUAAACU------A-GU-UACCGUCCACAGUGGAA...

C.jejuni 3  UUUCACUCGAAGCCGGAAUACUAAACU------N-GU-UACCGUCCACAGUGGAA...

C.jejuni 4  UUUCACUCGAAGCCGGAAUACUAAACU------A-GU-UACCGUCCACAGUGGAAUcA--GCGACUGGGG C. coli     UUUCACUCGAAGCCGGAAUACUAAACU-------A-GU-UACCGUCC...

C. laridis  UUUCACUCGAAGCCGGAAUACUAAACU------A-GU-UACCGUCCACAGUGGAA...

Probe 351         TGAGCTTCGGCCTTATGATTTGA------T-CA-ATGGCAGGTGTCACCTTAGTGGCCCGC
Probe 1134    TcGTGAGCTTCGGCCTTATGATTTGA------T-CA-ATGGCAGGc C. hyoint   UUUCACUCGAAGUCGGAAUGCUWAAUU------A(CG)UACCGCCCACAGUGGAAU...

C.sputorum  UUUCACUCGAAGCCCAAAUACCAAAUU------G-GU-UANGGUCCACAGUGGAA...

C. cryaero  ACUCAUUCGAAGCGGGGAUGCUAAAAU-------A-GC-UACCUUCCACAGUGGAUUUG--GCU...

W. succino  AUUCGCCUUAAGCCGGGACGCUAAACU------G-GC-UACCGUCCaCGGCGGAUGCA--GCGACnGGGG F. rappini  AUUCGCCUUAAGUCGGGAUACCMAAUU------G-GU-...

C. pylori   GUUUGCCUUAAGUCAGGAUGCUAAAUU------G-GC-UNCUGCCCACGGCACACA...
```

Legend. Organisms key and sequence notation are as in Tables 2A, 2B & 2C with the following additions: *C.jejuni 4* = CAMPMERG, an amalgam of 16S rRNA partial reverse transcription sequences from a number of *C. jejuni* strains (Lau et al., Systematic & Appl. Microbiol., 1987, 9:231–238). The parentheses around the CG dinucleotide in the *C. hyoint* sequence indicates that the bands identifying these two nucleotides migrated somewhat anomalously on sequencing gels.

TABLE 3

CYTODOT HYBRIDIZATIONS

| Genus. Species | Strain | Source | Probe 732 | Probe 999 | Probe 1104 | Probe 1105 | Probe 1130 | Probe 1132 | Probe 1133 | Probe 1134 |
|---|---|---|---|---|---|---|---|---|---|---|
| C. jejuni | 29428 | (1) | + | + | + | + | + | + | + | + |
| C. jejuni | 33560 | (1) | + | + | + | + | + | + | + | + |
| C. jejuni | N933 | (2) | + | + | + | + | + | + | + | + |
| C. jejuni | N941 | (2) | + | + | + | + | + | + | + | + |
| C. jejuni | R1227 | (2) | + | + | + | + | + | + | + | + |
| C. coli | 33559 | (1) | + | + | + | + | + | + | + | + |
| C. coli | 84-29 | (3) | + | + | + | + | + | + | + | + |
| C. coli | P1077 | (2) | + | + | + | + | + | + | + | + |
| C. laridis | 35223 | (1) | + | + | + | + | + | + | + | + |
| C. laridis | 11253 | (1) | + | + | + | + | + | + | + | + |
| C. laridis | UA487 | (4) | + | + | + | + | + | + | + | + |
| C. laridis | UA577 | (4) | + | + | + | + | + | + | + | + |
| C. laridis | UA603 | (4) | + | + | + | + | + | + | + | + |
| C. spp. (62 isolates) | clinical | (2,3,4) | 62+ | 62+ | 58+ | 62+ | 62+ | 62+ | 62+ | 62+ |
| C. fetus fetus | 33246 | (1) | + | + | − | + | + | + | + | − |
| C. fetus venerealis | 33561 | (1) | + | − | − | + | + | + | + | − |
| C. hyointestinalis | 35217 | (1) | + | − | − | + | − | − | − | − |
| C. hyointestinalis | UA625 | (4) | + | + | + | + | + | + | + | − |
| C. concisus | 33237 | (1) | + | + | + | + | − | − | − | + |
| C. mucosalis | 43264 | (1) | + | − | − | + | − | − | − | − |
| C. sputorum | 33562 | (1) | − | − | + | + | − | − | − | − |
| C. cinaedi | 35683 | (1) | − | + | + | + | + | + | − | + |
| C. fennelliae | 35684 | (1) | − | − | + | + | − | − | − | + |
| C. pylori | 43504 | (1) | − | − | − | + | − | − | − | − |

TABLE 3-continued

CYTODOT HYBRIDIZATIONS

| | | | Hybridization | | | | | | | |
|---|---|---|---|---|---|---|---|---|---|---|
| Genus. Species | Strain | Source | Probe 732 | Probe 999 | Probe 1104 | Probe 1105 | Probe 1130 | Probe 1132 | Probe 1133 | Probe 1134 |
| C. cryaerophila | 43157 | (1) | − | − | − | + | − | − | − | − |
| C. nitrofigilis | 33309 | (1) | − | − | − | + | − | − | − | − |
| C. fecalis | UA689 | (4) | + | − | + | + | + | + | + | − |
| C. fecalis | 33790 | (1) | − | + | − | + | − | − | − | − |
| Bacteriodes gracilis | 33236 | (1) | − | − | − | + | − | − | − | − |
| B. ureolyticus | 33387 | (1) | + | − | − | + | − | − | − | − |
| Wolinella recta | 33238 | (1) | + | − | − | + | − | − | − | − |
| W. curva | 35224 | (1) | + | − | − | + | − | − | − | − |
| W. succinogenes | 25943 | (1) | − | − | + | + | + | − | − | − |
| Pseudomonas aeruginosa | IG928 | (5) | − | − | − | − | − | − | − | − |
| Escherichia coli | N99 | (5) | − | − | − | − | − | − | − | − |
| Salmonella typhimurium | 23566 | (1) | − | − | − | − | − | − | − | − |

Legend:
Hybridization with cytodots of each strain are approximated for each probe as positive (+) or negative (−).
Positive signals vary from very strong (i.e., for *C. jejuni, C. coli* and *C. laridis* strains) to variable (e.g., non-*jejuni, coli* or *laridis Camphylobacter* strains) or quite weak (i.e., for the non-Campylobacter). The 62 clinical isolates have not all been typed to the species level, presumably most are *C. jejuni, C. coli* or *C. laridis* strains.
Sources for the listed bacterial strain are as follows:
(1) American Type Culture Collection, Rockville, MD
(2) Gary Doern, University or Mass. Med. Cntr., Worcester, MA
(3) H.J. Blaser, VA Medical Center Denver. CO
(4) Tanya Sanderos, Vermont Dept. of Health, Burlington, VT
(5) GTS in-house isolate

What is claimed is:

1. A method for detecting the presence of Campylobacter bacteria in a sample, comprising:
    a) obtaining at least one nucleic acid probe that hybridizes to 16S rRNA or rDNA of Campylobacter bacteria under stringent hybridization conditions and does not hybridize to 16S rRNA or rDNA of *Pseudomonas aeruginosa, Escherichia coli*, or *Salmonella typhimurium* under the same hybridization conditions, said probe consisting of an isolated nucleic acid and none, one, or both of a polynucleotide tail and a reporter group, said nucleic acid consisting of a sequence of nucleotides that is fully complementary or identical to at least ten consecutive nucleotides selected from any one of regions 124 to 225, 391 to 501, 973 to 1049, or 1424 to 1489 (using the *E. coli* position numbering convention) of the 16S rRNA of *Campylobacter jejuni* bacterial;
    b) contacting the sample with at least one of said probes under conditions that allow said probe to hybridize to rRNA or rDNA of Campylobacter, if present in said sample, to form probe/target duplexes; and
    c) detecting said duplexes as an indication of the presence of Campylobacter in said sample.

2. A method of claim 1, wherein said nucleic acid is fully complementary or identical to at least ten consecutive nucleotides selected from any one of probes 345, 346, 732, 999, 1104, 1105, 1130, 1132, 1133, 351, or 1134.

3. A method of claim 2, wherein said nucleic acid is fully complementary or identical to any one of probes 345, 346, 732, 999, 1104, 1105, 1130, 1132, 1133, 351, or 1134.

4. A method of claim 2, wherein said nucleic acid is fully complementary or identical to any one of probes 732, 999, 1104, 1105, 1130, 1132, 1133, or 1134.

5. A method of claim 1, wherein the sample is contacted with a set of at least two nucleic acid probes, wherein each of the probes in the set has a different nucleotide sequence.

6. A method of claim 5, wherein the sequence of nucleotides of a first probe in the set is fully complementary or identical to at least ten consecutive nucleotides of probe 346 or 732, and the sequence of nucleotides of a second probe in the set is fully complementary or identical to at least ten consecutive nucleotides of probe 345 or 999.

7. A method of claim 6, wherein the sequence of nucleotides of the first probe is fully complementary or identical to probe 732, and the sequence of nucleotides of the second probe is fully complementary or identical to probe 999.

8. A method of claim 5, wherein the sequence of nucleotides of a first probe in the set is fully complementary or identical to at least ten consecutive nucleotides of probe 1104, and the sequence of nucleotides of a second probe in the set is fully complementary or identical to at least ten consecutive nucleotides of probe 1105.

9. A method of claim 8, wherein the sequence of nucleotides of the first probe is fully complementary or identical to probe 1104, and the sequence of nucleotides of the second probe is fully complementary or identical to probe 1105.

10. A method of claim 5, wherein the sequence of nucleotides of a first probe in the set is fully complementary or identical to at least ten consecutive nucleotides or probe 1132 or 1133, and the sequence of nucleotides of a second probe in the set is fully complementary or identical to at least ten consecutive nucleotides or probe 1130.

11. A method of claim 10, wherein the sequence of nucleotides of the first probe is fully complementary or identical to probe 1132 or 1133, and the sequence of nucleotides of the second probe is fully complementary or identical to probe 1130.

12. A method of claim 1, wherein said nucleic acid consists of a sequence of nucleotides that is fully complementary or identical to at least ten consecutive nucleotides selected from any one of probes 999, 1132, 1133, or 1134.

13. An assay kit for detecting Campylobacter bacteria comprising a nucleic acid probe packaged in at least one container, wherein said probe hybridized to 16S rRNA or rDNA of Campylobacter bacteria under stringent hybridization conditions and does not hybridize to 16S rRNA or rDNA of *Pseudomonas aeruginosa, Escherichia coli,* or *Salmonella typhimurium* under the same hybridization conditions, said probe consisting of an isolated nucleic acid and none, one, or both of a polynucleotide tail and a reporter group, said nucleic acid consisting of a sequence of nucleotides that is fully complementary or identical to at least ten consecutive nucleotides selected from any one of regions 124 to 225, 391 to 501, 973 to 1049, or 1424–1489 (using the *E. coli* position numbering convention) of the 16S rRNA of *Campylobacter jejuni* bacteria.

14. A kit of claim 13, wherein said nucleic acid is fully complementary or identical to at least ten consecutive nucleotides selected from any one of probe 345, 346, 732, 999, 1104, 1105, 1130, 1132, 1133, 351, or 1134.

15. A kit of claim 14, wherein said nucleic acid is fully complementary or identical to any one of probes 345, 346, 732, 999, 1104, 1105, 1130, 1132, 1133, 351, or 1134.

16. A kit of claim 15, wherein said nucleic acid is fully complementary or identical to any one or probes 732, 999, 1104, 1105, 1130, 1132, 1133, or 1134.

* * * * *